United States Patent [19]

Stanners et al.

[11] Patent Number: 5,011,776

[45] Date of Patent: Apr. 30, 1991

[54] **SHUTTLE VECTOR, UTILIZING THE *E. COLI* ASPARAGINE SYNTHETASE GENE, AND CAPABLE OF DOMINANT TRANSFECTION AND AMPLIFICATION IN ANIMAL CELLS**

[75] Inventors: Clifford P. Stanners, Baie d'Urfé; Mireille Cartier, Pierrefonds, both of Canada

[73] Assignee: The Royal Institution for the Advancement of Learning (McGill University), Montreal, Canada

[21] Appl. No.: 154,912

[22] Filed: Feb. 11, 1988

[51] Int. Cl.[5] .................. C12N 15/64; C12N 15/85; C12N 15/69; C12N 5/10
[52] U.S. Cl. ..................... 435/172.3; 435/69.1; 435/70.1; 435/91; 435/240.2; 935/34; 935/55; 935/70; 935/60; 935/79
[58] Field of Search ............ 435/172.3, 41, 240.2, 435/252.8, 317; 935/23, 34, 55, 70, 71, 72

[56] References Cited

U.S. PATENT DOCUMENTS 4,656,134 4/1987 Ringold ......................... 435/91

OTHER PUBLICATIONS

Nakamura et al., Nucleic Acids Research vol. 19 #18 1981 pp. 4669–4676.
Cartier et al., Mol. and Cell. Biol. vol. 7 #5 (1987) pp. 1623–1628.
Chemical Abstracts, 98:192668s [(1983), Waye et al., J. Mol. Appl. Genet. 2(1), 69–82 (1983)].

*Primary Examiner*—Richard A. Schwartz
*Assistant Examiner*—S. L. Nolan
*Attorney, Agent, or Firm*—Dressler, Goldsmith, Shore, Sutker & Milnamow

[57] ABSTRACT

A shuttle vector capable of dominant transfection of both animal and bacterial cells and of amplification in animal cells has been constructed. This vector contains the cloned bacterial gene coding for asparagine synthetase; it is shown that animal cells bearing the vector can be selected for with a drug which inhibits the animal but not the bacterial asparagine synthetase. The vector and any linked genes can then be amplified using a drug which inhibits the bacterial synthetase. This vector is useful in the production of large quantities of specific biological products by animal cells. It may also be useful for the genetic transformation of plants.

1 Claim, 5 Drawing Sheets

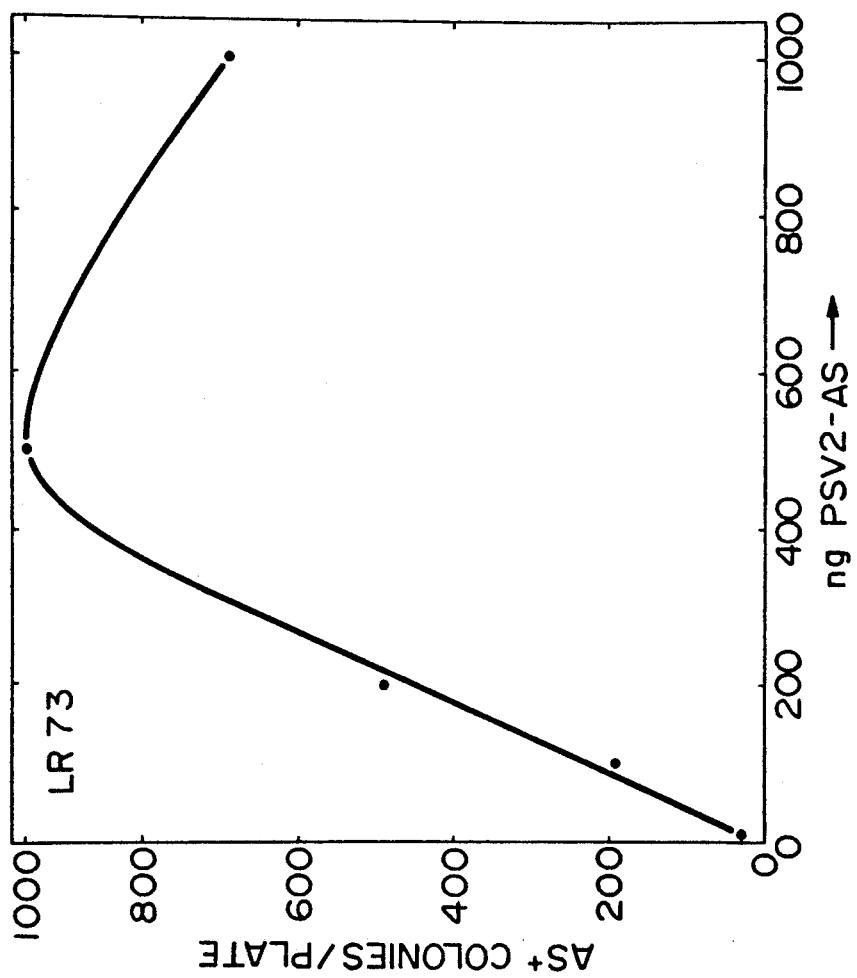

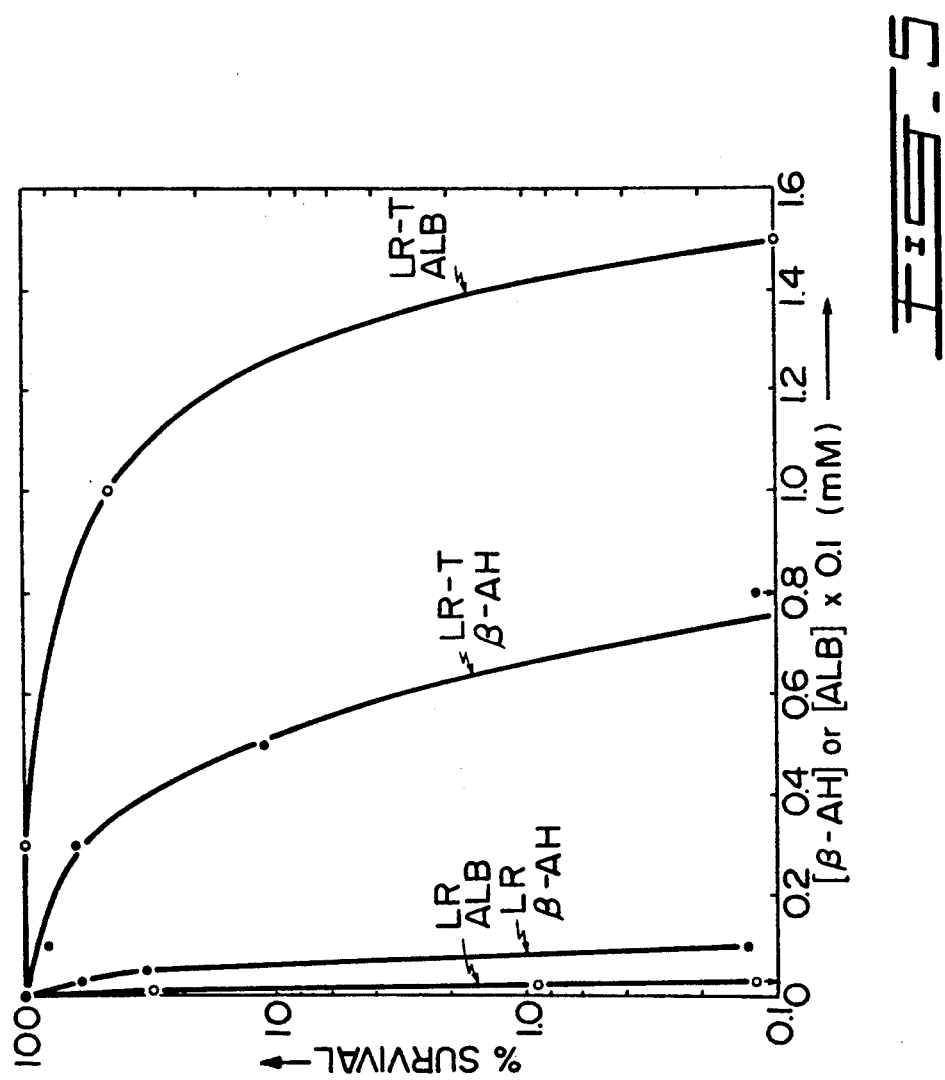

5,011,776

SHUTTLE VECTOR, UTILIZING THE *E. COLI* ASPARAGINE SYNTHETASE GENE, AND CAPABLE OF DOMINANT TRANSFECTION AND AMPLIFICATION IN ANIMAL CELLS

BACKGROUND OF THE INVENTION

The introduction of cloned nucleotide sequences into animal cells has greatly facilitated the study of the control and function of various eucaryotic genes. Bacterial-animal cell shuttle vectors, capable of selection and amplification as plasmids in bacteria and as episomal or integrated genetic elements in animal cells, are particularly convenient for this purpose. Such vectors require genes capable of conferring a selective advantage on both bacteria and animal cells harboring them. It is often the animal cell side of this requirement which is particularly difficult to meet, since, ideally, selection and amplification should be possible in many types of cells.

Up until now, the most commonly used systems used for these purposes were the neo genes selectable with the antibiotic G-418, the gpt gene selectable with mycophenolic acid, and the dhfr gene selectable with methotrexate. However, important drawbacks have been noted for each of these systems. Thus, neo and gpt cannot be amplified, dhfr is easily amplified but difficult to select in anything but dhfr⁻ recipients, and all of the markers require the use of mutagenic drugs for selection.

Therefore, a selectable marker for shuttle vectors possessing both efficient dominant animal cell transfection as well as strong amplification capabilities would be highly desirable.

SUMMARY OF THE INVENTION

In accordance with the present invention, there is provided a shuttle vector capable of dominant transfection and amplification in animal cells. This vector is generally characterized in that it comprises any suitable vector capable of selection and growth in bacterial cells and expression of inserted nucleotide sequences in animal cells, and the cloned *E.Coli* gene AsnA coding for asparagine synthetase production, said *E.Coli* AsnA gene being expressible in animal cells.

More particularly, the shuttle vector, pSV2-AS, of the present invention is constructed by inserting a cloned 2kb Pst I *E.Coli* genomic fragment containing the bacterial asparagine synthetase gene into the HindIII site of a pBR322-simian virus 40 vector, pSV2.

The present invention also relates to a method for dominant transfection and amplification of a vector containing an expressible gene in animal cells. This method is characterized by (1) inserting in an animal cell a shuttle vector comprising,
 (a) any suitable vector capable of selection and growth in bacterial cells and of expression of inserted nucleotide sequences in animal cells and,
 (b) the cloned *E.Coli* gene AsnA coding for asparagine synthetase production, said *E.Coli* gene being expressible in animal cells, thereby obtaining animal transfectants, containing said shuttle vector and the expressible gene, (2) selecting said animal transfectants containing said shuttle vector with a culture medium lacking asparagine and containing albizziin, (3) growing said animal cell transfectants in a culture medium containing increasing concentrations of β-aspartyl hydroxamate, thereby selecting animal cell transfectants containing large amounts of said shuttle vector and the expressible gene.

The efficiency of this vector is based on the fact that the bacterial asparagine synthetase enzyme is resistant to the drug albizziin, whereas the animal asparagine synthetase enzyme is strongly inhibited. Thus, cells which contain the vector can be selected by making their growth dependent on the bacterial asparagine synthetase enzyme. This is done using medium lacking asparagine and containing albizziin. Amplification of the vector in such cells can then be achieved by selection of cells with higher copy numbers of the vectors. This is accomplished by using a second drug, 8-aspartyl hydroxamate (8-AH) which inhibits the growth of the bacterial asparagine synthetase. Therefore, only cells which produce large amounts of the bacterial enzyme, can escape the inhibition caused by this second drug.

The novel shuttle vector of the present invention may be used in the production of biological products by animal cells in the following manner: the gene corresponding to the desired product may be inserted into the vector and mammalian cells containing high copy numbers of the vectors selected. These cells would then produce large amounts of the desired product. Furthermore, it is anticipated that the vector of the present invention may be used for the genetic transformation of plants.

The preparation and utility of the shuttle vector of the present invention will be better understood by referring to the following description.

IN THE DRAWINGS

FIG. 2 represents the efficiency of transfection of mutant animal cells deficient in AS, Jensen and CHO N3 cells, with pSV2-AS.

FIG. 4 represents the efficiency of transfection of wild type animal cells, i.e. LR-73 cells, with pSV2-AS.

FIG. 5 represents the sensitivity of LR-73 cells and LR-73 pSV2-AS transfectant cells to Albizziin and β-AH (β-aspartyl hydroxamate).

DETAILED DESCRIPTION OF THE INVENTION

Figure 1:
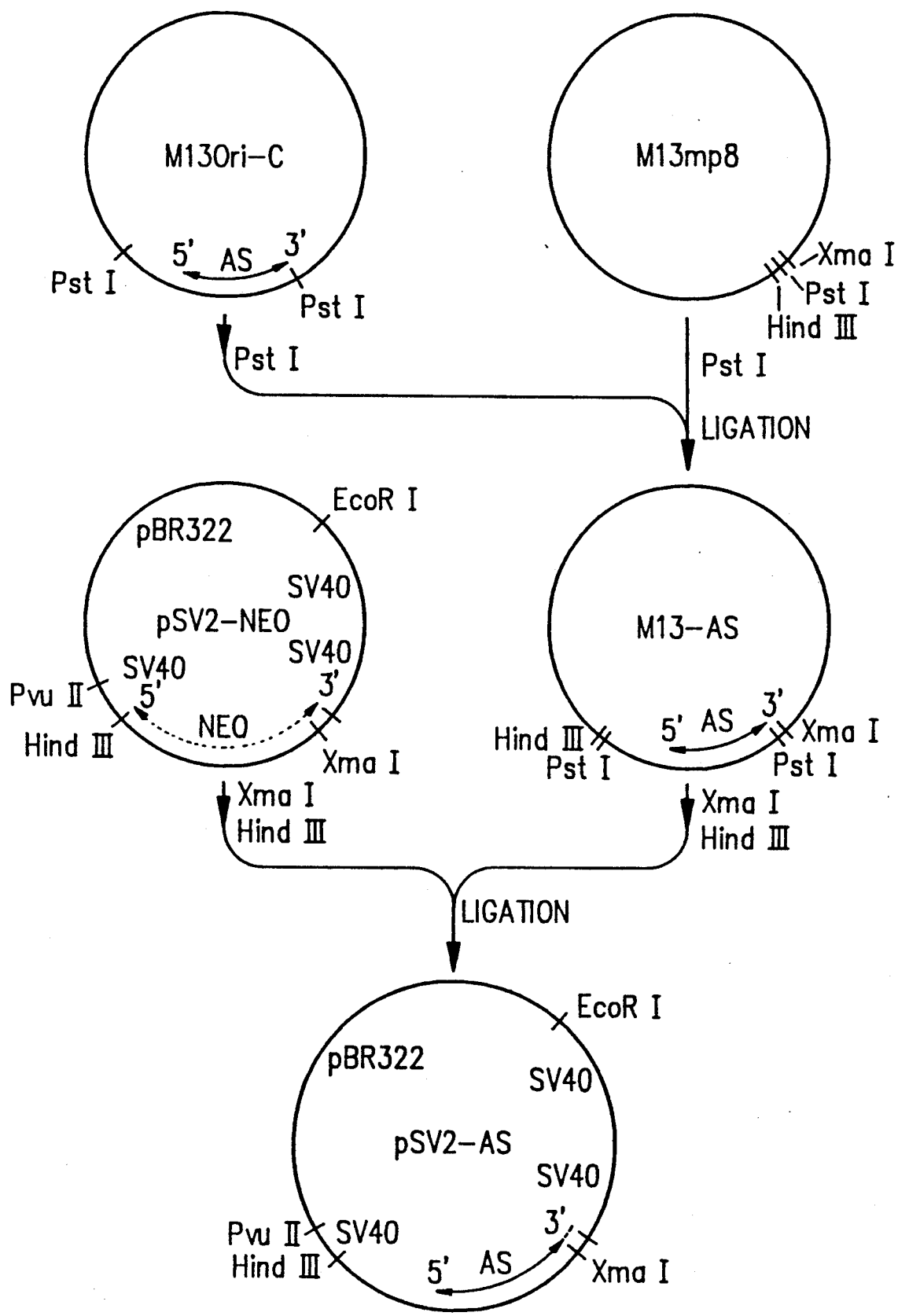
FIG. 1 represents the restriction endonuclease maps of the various plasmids used in the construction of pSV2-AS shuttle vector.

The present invention relates to a shuttle vector, pSV2-AS, which utilizes the *E.coli* gene, AsnA, coding for asparagine synthetase (AS), an enzyme which catalyzes the formation of asparagine from aspartic acid, for selection of animal cell transfectants. This vector allows one to obtain as many as 2 transfectants per ng of pSV2-AS per $10^6$ cells exposed, and is capable of both complementing animal cell AS⁻ mutants, thus allowing them to grow in asparagine-free medium, and of rendering normal AS⁺ animal cells highly resistant to the toxic drug albizziin. This resistance may be attributed to the fact that the *E.coli* enzyme utilizes the $NH_4^+$ ion as an amide donor, whereas the mammalian enzyme utilizes glutamine. Thus, albizziin is believed to inhibit the animal cell asparagine synthetase enzyme function by affecting the ability of the enzyme to transfer amide groups from glutamine.

Furthermore, both the animal cell and the bacterial AS enzyme are inhibited by β-aspartyl hydroxamate ( 8 -AH), a cytotoxic aspartic acid analogue. This inhibition permits the amplification of the bacterial sequences in pSV2-AS transfectants up to 1000 copies per haploid genome by selection in medium containing increasing concentrations of β-aspartyl hydroxamate. Thus, pSV2-AS can be readily used to insert and amplify a test nucleotide sequence in either AS⁻ or wild type AS⁺ animal cells.

The usefulness and efficiency of the vector of the present invention is apparent from the following. First, as is the case for any construct involving a bacterial gene which contains bacterial transcriptional and translational control sequences, the AS gene encoded in pSV2-AS can function in both bacterial and animal cells. Aside from allowing dominant transfection and amplification of test nucleotide sequences in AS⁺ cells, pSV2-AS also has the advantage of allowing transfection by complementation of AS⁻ cell mutants, which is relatively easy and inexpensive as it requires very little drug. Furthermore, amplification in such systems is readily achieved by the use of β-AH. Finally, another non negligible advantage of the present system, is that the selection of pSV2-AS does not involve the use of drugs which are mutagenic.

(a) Construction of the shuttle vector

In order to increase the efficiency of transfection of AS⁻ or AS⁺ mammalian cells by the bacterial AS gene originally cloned in a microbial vector, a fragment containing the bacterial AS gene is introduced into an expression site in a bacterial-animal cell shuttle vector by standard cloning techniques such as ligation of the fragment to vector DNA cut with a restriction endonuclease at the expression site. Although it is contemplated that various bacterial-animal cell shuttle vectors may be used, the pBR322-simian virus 40 recombinant vector (pSV2) is preferred.

(b) Cell lines

The mammalian cell lines that are required in the context of the present invention are either cell lines which are defective in asparagine synthetase genes or wild-type cell lines carrying the mammalian AS gene. Various mammalian cell lines meeting these requirements are available. The Jensen rat sarcoma cell line as well as the N3 Chinese hamster ovary mutant, both lacking AS activity and AS⁺ cell lines such as LR-73, HeLa, Rat 2, NIH 3T3 and NRK may be used in the context of the present invention, although it will be appreciated that the use of a wide variety of mammalian cells could be contemplated.

(c) Transfection technique

Transfection of mammalian AS⁻ or AS⁺ cells with the shuttle vector of the present invention is effected by exposing cells to the vector containing the bacterial AS gene in quantities ranging between 1 ng and 50 ug per $10^6$ cells. Among the available techniques, the calcium phosphate precipitation method may be used. Cell colonies which have acquired and express the bacterial AS gene may be selected by growth in asparagine-free medium containing an agent which will lead to the death of the non-transformed animal cells. In the context of the present invention, concentrations of β-aspartyl hydroxamate ranging from 0.1 mM to 10 mM, albizziin at concentrations varying between 0.5 mM and 50 mM, and possibly other cytotoxic aspartic acid analogues, which inhibit mammalian AS activity may be used. Low levels of β-AH, for example 0.1 mM, are used for AS⁻ cells in spite of their absolute requirement for asparagine because of the relatively high frequency of partial AS⁺ revertants in AS⁻ cell populations. Thus, the inclusion of low levels of this analogue in the selection medium reduces the frequency of revertants below the level of detection.

(d) Amplification of the AS gene in transfectants

Bacterial-animal cell shuttle vectors are more useful if they can be amplified in their animal cell recipients. Thus, amplification may be achieved in mammalian AS⁺ transfectants by selection with increasing concentrations of a cytotoxic drug which inhibits AS activity such as β-AH in concentrations varying between 0.1 mM and 10 mM. Therefore, cells containing small amounts of the vector will die because their production of asparagine synthetase will be too low to allow survival. However, cells containing large amounts of the vector will produce more asparagine synthetase thus enabling them to survive in the presence of the cytotoxic drug. As the concentration of the cytotoxic analogue is increased, only the cells containing large amounts of the vector will remain.

The present invention will be more readily illustrated by referring to the following examples, which do not intend to limit the scope of the present invention thereto.

EXAMPLE 1

Construction of pSV2-AS vector

A 2-kilobase (kb) PstI-PstI fragment taken from the plasmid M13 Ori-C and containing the 1-kb asparagine synthetase gene at its 3' end was first subcloned into the PstI site in vector M13mp8 to take advantage of the multiple unique restriction enzyme sites in the cloning region of that vector. The resulting vector was labelled M13-AS. The 2-kb PstI fragment was then removed from M13-AS by digestion with HindIII and XmaI and inserted into pSV2neo from which most of the neo gene had been excised by digestion with the same enzymes. The resultant vector, pSV2-AS, places the simian virus 40 (SV40) early transcriptional promoter about 1000 base pairs (bp) upstream from the translational initiator ATG codon for the bacterial AS gene followed by the complete AS gene and then by 180 bp of residual neo gene and the SV40 transcriptional termination signals of the pSV2 vector. The restriction endonuclease map of the pSV2-AS vector as well as the maps of the starting and intermediate plasmids can be visualized in FIG. 1.

EXAMPLE 2

Preparation of the mammalian cell cultures

The following mammalian cell lines were used in the context of the present invention: AS⁺ cell lines, which are cell lines containing a gene coding for the mammalian asparagine synthetase: HeLa (human), Rat 2 (rat), NIH 3T3 (mouse), NRK (rat) and LR-73 (a Chinese hamster ovary line described by Pollard et al in 1979, J. Cell. Physiol. 98:571-585); and two AS⁻ cell lines: a Jensen rat sarcoma cell line which has been described by Waye & Stanners in 1983 Mol. Appl.

Genet. 2:69-82 as well as a Chinese hamster ovary (CHO) mutant CHO-N3 lacking AS activity which has been described by Waye & Stanners in 1979 Somatic Cell Genet. 5:625-639. The Jensen rat sarcoma cell line was grown in monolayer culture in α-minimal essential medium (α-MEM) described by Stanners et al. in 1971 Nature (London) 230:52-54 supplemented with 6.5% calf serum and 3.5% fetal calf serum. All the other cell lines used in the present invention were grown in monolayer culture with β-MEM supplemented with 10% fetal calf serum.

EXAMPLE 3

Transfection of the pSV2-AS shuttle vector to various AS− and AS+ mammalian cell lines DNA transfections were performed by using the calcium phosphate precipitate method described by Graham et al. in 1980 Progress in Clinical and Biological Research: Introduction of Macromolecules to Viable Mammalian cells, pages 3–25. Cells were first seeded into 80-cm$^2$ flasks at a density of $2 \times 10^6$ to $3 \times 10^6$ cells per flask. Two days later, these cultures were used to provide cells in late exponential phase, which were placed in 100-mm plastic petri dishes at 6 $6 \times 10^5$ to $8 \times 10^5$ cells per plate. The next day, 1 ml of a calcium phosphate solution containing the specified amount of plasmid and 10 ug of carrier DNA was added to each plate. The carrier DNA used was high molecular-weight genomic DNA extracted from the cell line CHO N3 by the protocol described by Maniatis et al. in 1982 Molecular Cloning: Laboratory Manual, Cold Spring Harbor Laboratories, Cold Spring Harbor, NY. The cells were then incubated at 37o C for 12 to 16 hours, at which point the medium was replaced. After 48 hours of incubation to allow expression, selection was applied to the cells in the following manner: the cells were washed at 37o C with β-MEM supplemented with 1% dialyzed serum and lacking asparagine and were incubated for about an hour; then the selective medium indicated below was applied. In some cases, the cultures were trypsinized at this stage and reseeded at $10^6$ cells per 100-mm plastic petri dish. The medium was changed every 3 to 4 days and, after about two weeks of incubation at 37° C., the cells were fixed with 10% Formalin and stained with a 0.1% solution of methylene blue. Colonies visible to the unaided eye (about 50 cells or more) were counted. All transfections were performed in triplicate.

For both Jensen and N3 cell lines, the selective medium used was α-MEM lacking asparagine, with 100 ug of glutamine per ml, 10% dialyzed serum, and 0.1 mM β-aspartyl hydroxamate (β-AH, obtained from Sigma Chemical Co). For all other wild-type AS+ cell lines, the selective medium consisted of α-MEM lacking asparagine, with 30 ug of glutamine per ml, 0% dialyzed fetal calf serum, and albizziin at concentrations varying between 2 and 10 mM.

Figure 2:
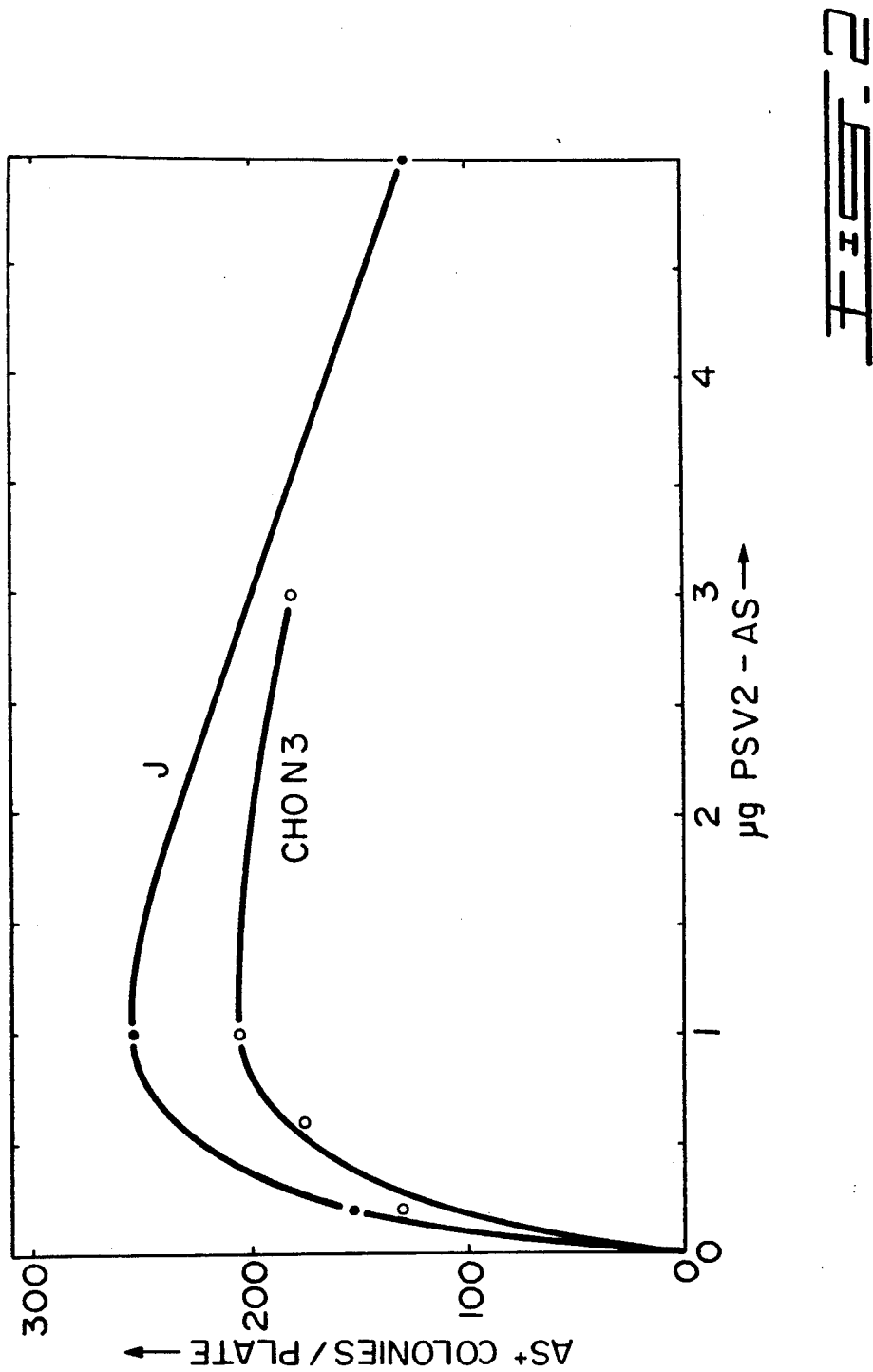

The results shown in FIG. 2 indicate peak transfection frequencies of 200 AS+ colonies per ug of DNA per $10^6$ cells for CHO N3 AS− cells and 260 AS+ colonies per ug of DNA per $10^7$ cells for Jensen AS− The purely microbial construct, M13-AS which is demonstrated in FIG. 1, produced no AS+ colonies when applied to either cell line in this particular experiment. The average transfection frequency for pSV2-AS applied to Jensen AS− cells in repeated experiments was 350 AS+ colonies per ug of DNA per $10^6$ cells. It is to be noted that the pSV2-AS construct is still capable of transformation of the bacterial AS− mutant JK1 which was described by Cedar et al. in J. Biol. Chem. 244:4112–4121, with an efficiency of about $10^4$ AS+ colonies per ug of DNA, indicating continued function of the AS gene in a bacterial milieu.

Dominant transfections with pSV2-AS were performed on the AS+ cell lines, HeLa, Rat 2, NIH 3T3, NRK and LR-73 using the calcium phosphate precipitation method described above, except for the fact that the transformed AS+ cell lines were subjected to selection with various concentrations of albizziin.

When LR-73 is transfected with various amounts of pSV2-AS and subjected to selection with albizziin at 2mM, large colonies are obtained with a linear dose-response curve up to 500 ng of pSV2-AS, with a sensitivity of approximately 2 colonies per ng of pSV2-AS per $10^6$ cells as shown in FIG. 4. This contrasts with the fact that non transformed LR-73 cells are completely unable to form colonies in the selective medium used (no asparagine, plus albizziin and glutamine concentrations of 2 mM and 30 ug/ml, respectively).

Furthermore, when one of the LR-73 transfectant colonies is picked and its sensitivity to albizziin and β-AH is compared with that of its non-transfected LR-73 parent, the D10 dose giving 10% colony survival of albizziin for this transfected colony is 13 mM compared with 0.13 mM for non-transfected LR-73, a 100-fold increase, whereas that of β-AH is 0.5 mM compared with 0.06 mM for non-transfected cells, a 8-fold increase as seen in FIG. 5. The greater increase seen with albizziin confirms the fact that acquisition of the bacterial AS confers on the mammalian cells strong resistance to this drug. Transfection results for the various mammalian cell lines are summarized in Table 1.

TABLE 1

| Cell line | Efficiency of transfection of various cell lines with pSV2-AS | | |
|---|---|---|---|
| | Selective agent | Concn (mM) | AS+ colonies per ug of DNA per $10^6$ cells[a] |
| Jensen | β-AH | 0.1 | 350 |
| CHO N3 | β-AH | 0.1 | 205 |
| LR-73 | ALB[b] | 2 | 691 |
| HeLa | ALB | 6 | 174 |
| Rat 2[c] | ALB | 8 | 73 |
| NIH 3T3[c] | ALB | 10 | 47 |
| NRK | ALB | 4 | 4 |

[a] The entries represent the average of several experiments, except for HeLa and NIH 3T3 cells, which were for one experiment only.
[b] ALB, Albizziin.
[c] Before selection was applied, cells were trypsinized and replated at $10^6$ cells per petri dish.

EXAMPLE 4

Amplification of the pSV2 AS transfected constructs

Transfectant clones derived from AS− mammalian cells capable of growth in medium containing 0.1 mM β-AH were picked and cultured in medium containing increasing concentrations of β-AH starting at 0.2 mM and increasing in successive steps of 0.2 mM up to 1.5 mM. From this concentration up to 5 mM β-AH, the steps were usually 1mM. Cultures were seeded at about $2 \times 10^6$ cells per 80-cm$^2$ tissue culture flask and incubated at a given concentration of drug until they grew to confluence, which required 2 to 3 weeks for Jensen transfectants.

Figure 3:
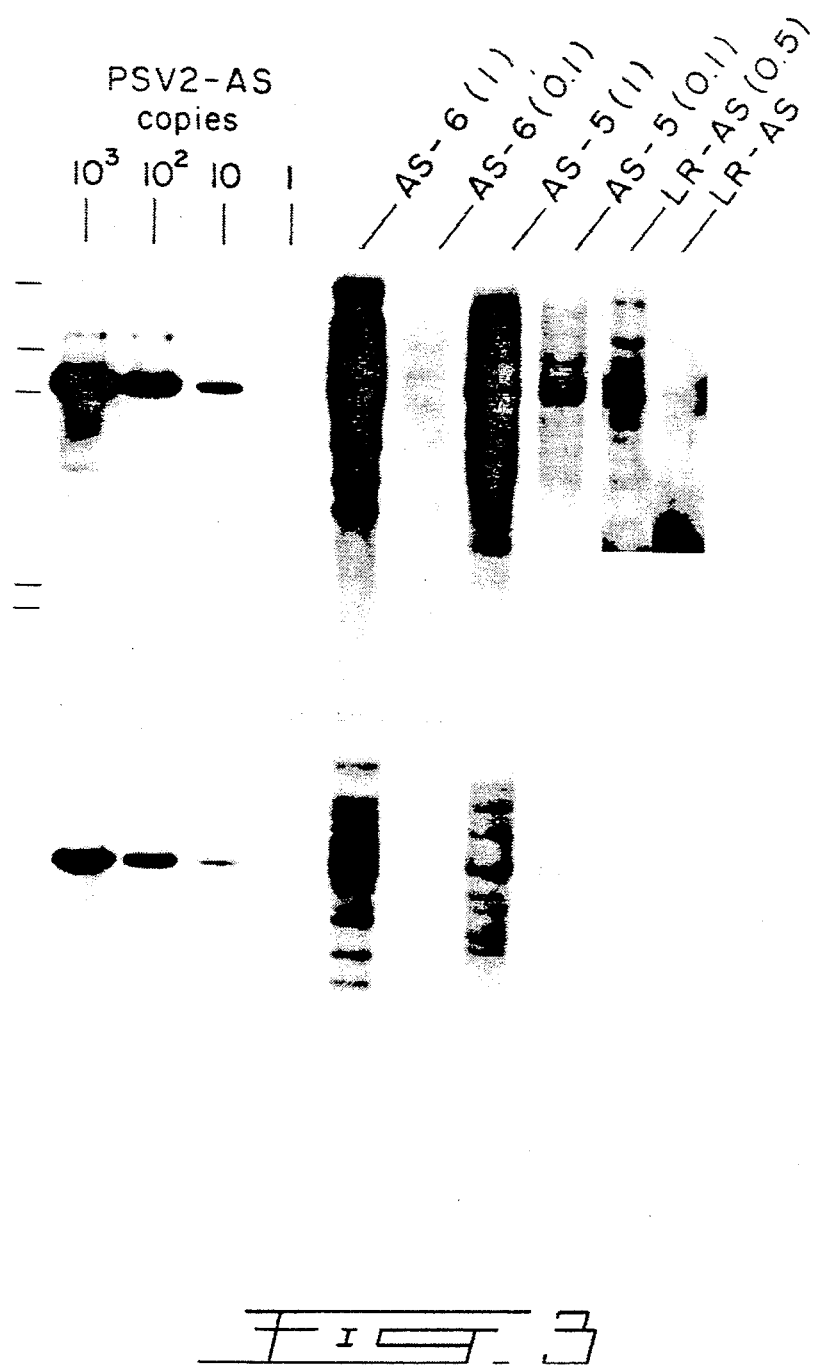
FIG. 3 represents autoradiographic film exposures of amplified AS sequences in mammalian transfectants.

Two Jensen transfectants, AS−5 and AS−6, obtained with pSV2-AS were subjected to selection with increasing concentrations of β-AH until they became resistant to 1 mM β-AH. High-molecular-weight genomic DNA was then isolated from the specified cell lines by the procedure described by Maniatis et al. in 1982, Molecular Cloning: A Laboratory Manual., Cold Spring Harbor Laboratory, Cold Spring Harbor, NY. A 10 ug portion of DNA was then digested with EcoRI, electrophoresed on a 1% agarose gel, and transferred to nitrocellulose. The blot was then hybridized with the nick-translated or random primer-labeled radioactive, denatured, replicative form of M13-AS in the presence of 50% formamide, 5 X SSPE, 1 X Denhardt solution, 0.1% sodium dodecyl sulfate, and 10% dextran sulfate at 42o C for 15 hours. The filter was then washed three times for 15 minutes, each at room temperature: twice with 2 X SSC (1 X SSC is 0.15 M NaCl plus 0.015 M sodium citrate)-0.1% sodium dodecyl sulfate and once with 0.5 X SSC-0.1% sodium dodecyl sulfate. FIG. 3 summarizes the results of these analyses.

By using an internal calibration with pSV2-AS on the same blot, it can be estimated that AS-5 (0.lmM $\beta$-AH) contained about 30 or 50 copies of pSV2-AS at up to 10 sites in the genome. Integration of the circular pSV2-AS at various sites in the carrier DNA or transfectant genome would give two bands for each site after EcoRI digestion (there is only one EcoRI site in pSV2-AS) only if the breakpoint for recombination was in the 2-kb AS$^-$-containing fragment included in the probe. Thus 10 bands would indicate 5 to 10 integration sites. The very dark band at the exact size of pSV2-AS could be due to multiple copies at any of the integration sites in a head-to-tail tandem array. The amplified AS-5 (1 mM $\beta$-AH) showed about a 10-fold amplification of most of the bands, giving a final copy number of 300 to 500 per genome. AS-6 (0.1 mM $\beta$-AH), on the other hand, contained about 5 to 10 copies per genome in even more bands, most of which were amplified in AS-6 (1 mM $\beta$-AH) 100-fold to a final copy number of 500 to 1000 per genome. These results show that pSV2-AS can be readily amplified in such transfectants.

Total RNA from the parental Jensen cells, from AS-5 (5 mM $\beta$-AH), and from AS-6 (lmM $\beta$-AH), was analyzed by the Northern blot procedure, again with M13-AS as a radioactive hybridization probe. The results showed no AS mRNA for the Jensen cells and two prominent AS mRNA bands for both of the transfectants, indicating strong transcription of the integrated and amplified pSV2-AS constructs.

It was demonstrated that the AS$^-$6 (0.lmM $\beta$-AH) was extremely resistant to albizziin. In fact, significant growth reduction of AS$^-$6 by albizziin could not be obtained even at doses as high as 20mM. Similar results were obtained for pSV2-AS transfectants of wild-type AS$^+$cells as shown in FIG. 5.

Amplification was also achieved in LR-73 transfectants from selection in medium containing 0.5 mM $\beta$-AH with results shown in FIG. 3.

Thus, amplification of the vector is also possible in wild-type cells containing endogenous mammalian AS enzyme.

It seems likely that the above results are due to resistance of the bacterial AS enzyme to albizziin. The effect has been exploited to develop a method for selection of bacterial AS transfectants of a wide range of normal mammalian AS$^+$cells.

What is claimed is:

1. A method for dominant selection and amplification of a vector in animal cells which are asparagine independent for growth, said method comprising,
   (1) transforming an animal cell with a shuttle vector comprising,
      (a) DNA sequences which render said vector capable of selection and growth in bacterial cells and expression of inserted nucleotide sequences in animal cells, and
      (b) the *E.Coli* gene AsnA coding for asparagine synthetase, and
      (c) an optional heterologous gene for which high level expression is desired,
   (2) selecting transformed cells containing said shuttle vector by growing the cells in a culture medium lacking asparagine and containing albizziin, wherein cells expressing the *E.Coli* AsnA gene are resistant to albizziin,
   (3) selecting transformed cells containing multiple copies of said shuttle vector by growing said transformed cells in a culture medium containing increasing concentrations of $\beta$-aspartyl hydroxamate.

* * * * *

UNITED STATES PATENT AND TRADEMARK OFFICE
CERTIFICATE OF CORRECTION

PATENT NO. : 5,011,776                                    Page 1 of 2
DATED      : April 30, 1991
INVENTOR(S) : Clifford P. Stanners & Mireille Cartier It is certified that error appears in the above-identified patent and that said Letters Patent is hereby corrected as shown below:

Col. 2, line 16,   "8-aspartyl" should be --$\beta$-aspartyl--;

Col. 2, line 17,   "(8-AH)" should be --($\beta$-AH)--;

Col. 3, line 2-3,  "(8-AH)" should be --($\beta$-AH)--;

Col. 4, line 62,   "Genet." should immediately follow "Appl." on line 61 above;
(delete paragraph indention)

Col. 5, line 3,    "$\beta$-MEM" should be --$\alpha$-MEM--;

Col. 5, line 17,   delete the second instance of "6";

Col. 5, line 26,   "37oC" should be --37°C--;

Col. 5, line 30,   "37oC with $\beta$-MEM" should be --37°C with $\alpha$-MEM--;

UNITED STATES PATENT AND TRADEMARK OFFICE
CERTIFICATE OF CORRECTION

PATENT NO. : 5,011,776

DATED : April 30, 1991

INVENTOR(S) : Clifford P. Stanners & Mireille Cartier

It is certified that error appears in the above-identified patent and that said Letters Patent is hereby corrected as shown below:

Col. 5, line 48, "0%" should be --10%--;

Col. 7, line 6, "42oC" should be --42°C--.

Signed and Sealed this

Thirteenth Day of October, 1992

Attest:

DOUGLAS B. COMER

Attesting Officer

Acting Commissioner of Patents and Trademarks